(12) United States Patent
Li et al.

(10) Patent No.: US 12,712,379 B2
(45) Date of Patent: Aug. 18, 2026

(54) METHOD AND SYSTEM FOR UNINTERRUPTED POWER SUPPLY SWITCHING FOR A PUMP DRIVE

(71) Applicant: Lifemotion Medical Technology Co., Ltd., Shenzhen (CN)

(72) Inventors: Yijiang Li, Shenzhen (CN); Bisheng Liu, Shenzhen (CN)

(73) Assignee: LIFEMOTION MEDICAL TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 19/224,502

(22) Filed: May 30, 2025

(65) Prior Publication Data

US 2025/0385541 A1 Dec. 18, 2025

(30) Foreign Application Priority Data

Jun. 13, 2024 (CN) ......................... 202410756280.2

(51) Int. Cl.
*H02J 9/06* (2006.01)
*A61M 1/14* (2006.01)
(Continued)

(52) U.S. Cl.
CPC ............... *H02J 9/06* (2013.01); *A61M 1/155* (2022.05); *A61M 1/1698* (2013.01); *H02J 7/80* (2026.01);
(Continued)

(58) Field of Classification Search
CPC ...... H02J 9/06; H02J 7/80; H02J 9/068; H02J 13/14; H02J 9/061; H02J 1/086;
(Continued)

(56) References Cited

U.S. PATENT DOCUMENTS 11,070,080 B1 * 7/2021 Davis ...................... H02J 9/068
2019/0125965 A1 5/2019 Mou et al.
(Continued)

FOREIGN PATENT DOCUMENTS

CN 107842589 A 3/2018
CN 110636873 B 12/2019
(Continued)

OTHER PUBLICATIONS

Extended European Search Report issued in EP25182814.1, mailed Oct. 27, 2025.

*Primary Examiner* — Rexford N Barnie
*Assistant Examiner* — Thai H Tran
(74) *Attorney, Agent, or Firm* — Nelson Mullins Riley & Scarborough LLP

(57) ABSTRACT

The present application provides a method and system for uninterrupted power supply switching for a pump driver. According to the electrical connection relationships among the devices in the system to which the method is applied, and the corresponding determination method of whether a control host switches normally, redundant power supply for the pump drive can be achieved. When one or more power supply devices supply power simultaneously, the types of all power supply devices can be fully identified, and during a power supply switching process, accurate determination and timely communication connection establishment with the pump drive can be achieved, avoiding abnormal alarms being triggered by the pump drive during or after the power supply switching process, thereby ensuring uninterrupted continuous operation of the pump drive.

9 Claims, 9 Drawing Sheets

(51) Int. Cl.
*A61M 1/16* (2006.01)
*H02J 7/80* (2026.01)

(52) U.S. Cl.
CPC ..... *A61M 2205/14* (2013.01); *A61M 2205/18* (2013.01); *A61M 2205/3327* (2013.01); *A61M 2205/3569* (2013.01); *A61M 2205/502* (2013.01); *A61M 2205/8206* (2013.01)

(58) Field of Classification Search
CPC ................ A61M 1/155; A61M 1/1698; A61M 2205/14; A61M 2205/18; A61M 2205/3327; A61M 2205/3569; A61M 2205/502; A61M 2205/8206
See application file for complete search history.

(56) References Cited

U.S. PATENT DOCUMENTS

2020/0003217 A1 1/2020 Wilds
2020/0182249 A1 6/2020 Mayleben
2021/0271272 A1* 9/2021 Vo .......................... G05B 15/02
2021/0361930 A1 11/2021 Johnson
2023/0241371 A1 8/2023 Le duc de Lillers
2023/0381411 A1 11/2023 Xu

FOREIGN PATENT DOCUMENTS

CN 111315423 A 6/2020
CN 116568361 A 8/2023
JP 6010808 B2 * 10/2016 .............. H02J 7/865

* cited by examiner

METHOD AND SYSTEM FOR UNINTERRUPTED POWER SUPPLY SWITCHING FOR A PUMP DRIVE

CROSS REFERENCE TO RELATED APPLICATIONS

The present application claims priority to Chinese Application No. 202410756280.2, filed Jun. 13, 2024, the entire disclosure of which is hereby incorporated by reference.

TECHNICAL FIELD

Embodiments of the present application belong to the technical field of power supply, and particularly relate to a method and system for uninterrupted power supply switching for a pump drive.

BACKGROUND ART

In clinical emergency treatment of critically ill patients with severe cardiopulmonary failure, extracorporeal membrane oxygenation (ECMO) is used to provide continuous extracorporeal respiratory and circulatory support for the patient, so as to gain more valuable time for emergency rescue. The core components of extracorporeal membrane oxygenation (ECMO) are the artificial lung (also called membrane lung or oxygenator) and artificial heart (also called blood pump, power pump, or pump drive). During the operation of the system, the patient's blood needs to be drawn out of the body through tubing, then pumped through the membrane lung for oxygenation by the blood pump, and finally delivered back into the body.

With the continuous improvement of extracorporcal artificial lung and artificial heart technologies, ECMO can be maintained for a longer period of time, which also provides a prerequisite for the application of ECMO in the treatment of patients with cardiopulmonary failure, especially for patients with severe cardiopulmonary failure caused by COVID-19, if ECMO can be used to maintain life for several days, dozens of days, or even longer, it will save more patients' lives.

In the ECMO system, the device to be powered (i.e., the pump drive) is usually powered by a power supply device. When the power supply from the control host fails and cannot provide power to the device to be powered (i.e., the pump drive), a battery can be used to directly provide emergency power to the pump drive. When the battery is depleted and needs to be replaced or a new control host needs to be reconnected, the device to be powered (i.e., the pump drive) may experience power outage and pump stoppage again. The pump stoppage operation increases the complexity of clinical operations and also increases the risk of patient treatment. In addition, in the existing technology, as disclosed in Patent CN115501403A, in order to improve safety performance, the device to be powered (i.e., the pump drive) may establish real-time communication monitoring with the control host. During a switching process of the power supply device or after the switching is completed, communication with the device to be powered (i.e., the pump drive) may be interrupted, resulting in abnormality alarms.

SUMMARY OF THE INVENTION

In order to solve or alleviate the situation in the existing technology where, when the power supply from the control host fails and cannot provide power to the device to be powered (i.e., the pump drive), a battery can be used to directly provide emergency power to the pump drive, and when the battery is depleted and needs to be replaced or a new control host needs to be reconnected, the device to be powered (i.e., the pump drive) may experience power outage and blood pump stoppage again, and the blood pump stoppage operation increases the complexity of clinical operations and also increases the risk of patient treatment, and additionally, during the switching process of the control host or after the switching is completed, communication with the device to be powered (i.e., the pump drive) may be interrupted, resulting in abnormality alarms.

In a first aspect, an embodiment of the present application provides a method for uninterrupted power switching for a pump drive, the method is applied to a system, the system comprises one or more power supply devices, a pump drive, a connector, and a display unit, wherein the one or more power supply devices are electrically connected to the pump drive via the connector for supplying power to the pump drive, the pump drive is connected to the display unit, the power supply devices comprise a control host or a battery, the method comprising:

- when the one or more power supply devices establish a connection with the pump drive via the connector, a control unit in the connector establishing a communication connection with the pump drive;
- the control unit identifying a type of the power supply device connected thereto, and if the control unit identifies that the connected power supply device comprises a control host, the control unit sending a communication establishment instruction to the pump drive, and the pump drive sending a communication connection request to the power supply device via the control unit to establish a real-time communication connection between the pump drive and the power supply device; and
- when the control host and the battery simultaneously supply power to the pump drive via the connector, the control unit in the connector establishing a real-time communication connection with the pump drive, when the control unit determines that the control host is switched normally, the control unit sending a control host normal switch signal to the display unit and/or the pump drive to avoid a false alarm of the system; when the control unit determines that the control host has a communication abnormality, the control unit sending a control host communication abnormality signal to the display unit and/or the pump drive, and the system issues an alarm signal.

As an embodiment of the present application, the control unit determining that the control host is switched normally comprises:

- when the control unit detects that a communication between the control host and the control unit is disconnected within a preset time, and a power supply voltage of the connector connected to the control host is lower than a preset value or is 0, the control unit determining that the control host is switched normally, and sending the control host normal switch signal to the display unit and/or the pump drive.

As an embodiment of the present application, the control unit determining that the control host has the communication abnormality comprises:

- when the control unit detects that a communication between the control unit and the control host is disconnected within a preset time, and there is a power supply voltage at the connector connected to the control host, determining that the control host has the communication abnormality and the control host is supplying power to the pump drive normally; and the control unit sending the control host communication abnormality signal to the display unit and/or the pump drive.

As an embodiment of the present application, the control unit identifying the type of the power supply device connected thereto comprises:

the control unit sending a first communication connection request to the connector connected to the power supply device, and if the control unit can establish a real-time communication connection with the battery, determining the type of the power supply device supplying power to the pump drive to be the battery, and the control unit reading a power level of the battery;

if the control unit cannot establish a communication connection with the battery, the control unit sending a second communication connection request to the power supply device, if the control unit can establish a communication connection with the control host, determining that the type of the power supply device supplying power to the pump drive to be the control host, and determining whether the control unit establishes a communication connection with only one control host; if a communication connection is established with only one control host, the control unit establishing a communication connection with that one control host; if a communication connection is not established with only one control host, the control unit selecting any one of the control hosts to establish a communication connection with the control unit.

As an embodiment of the present application, the control unit in the connector establishing the real-time communication connection with the pump drive comprises:

determining, by the control unit, whether the pump drive is connected, and if so, the control unit sending a communication connection to the pump drive; and the control unit determining whether the pump drive has a communication return signal, and if so, the control unit establishing the real-time communication connection with the pump drive; if not, the system issuing an alarm.

As an embodiment of the present application, the method further comprises:

when the power supply device supplying power to the pump drive comprises a battery, the control unit reading battery parameters and calculating a battery endurance parameter based on the battery parameters, then sending the battery endurance parameter to the display unit; and when the battery endurance parameter is less than a preset threshold, the display unit issuing an alarm to remind a user to check for faults.

As an embodiment of the present application, the method further comprises:

when the power supply device supplying power to the pump drive comprises a battery, necessarily determining whether the number of input batteries is 2; if it is determined that the number of input batteries is not 2, setting all battery parameters of unconnected batteries to be 0 by the control unit, the control unit reading the battery parameters and calculating a battery endurance parameter based on the battery parameters; if the number of input batteries is 2, the control unit reading the battery parameters and calculating the battery endurance parameter based on the battery parameters;

the method for calculating the battery endurance parameter is as follows:

the control unit respectively reading a remaining capacity, a total capacity, and an output current of each battery, and then using the following formulas to respectively calculate a remaining power supply time and a remaining power percentage of the batteries;

Battery remaining time=sum of remaining capacities of each battery÷sum of output currents of each battery;

Battery remaining power percentage=battery remaining capacity÷battery total capacity.

As an embodiment of the present application, the method further comprises:

the control unit determining whether the battery endurance parameter is within a reasonable range;

if the battery endurance parameter is within the reasonable range, the control unit performing sliding average filtering processing on the battery endurance parameter of each battery respectively and then sending to the display unit for display; if the battery endurance parameter is not within the reasonable range, the control unit re-reading the battery parameters of the battery corresponding to the battery endurance parameter that is not within the reasonable range.

Compared with the existing technology, an embodiment of the present application further provides a method for uninterrupted power switching for a pump drive. According to the electrical connection relationships among devices in the system to which the method is applied, and the corresponding determination method for whether the control host is switched normally, redundant power supply for the pump drive can be realized. When one or more power supply devices are supplying power simultaneously, all types of power supply devices can be fully identified, and during a power supply switching process, communication connection with the pump drive can be accurately determined and established in a timely manner, thereby avoiding abnormality alarms triggered by the pump drive during or after the power switching process, and ensuring uninterrupted continuous operation of the pump drive.

In a second aspect, an embodiment of the present application provides a system for executing the method set forth in the first aspect. The system comprises a control host, a battery, a pump drive, a connector, a display unit, and a human-machine interaction unit. The control host and/or the battery are electrically connected to the pump drive via the connector. The pump drive is connected to the display unit, and the display unit is configured to display an operating status, operating parameters, and abnormality alarm information of the pump drive.

The human-machine interaction unit is electrically connected to the control host, and a control command input from the outside is transmitted to the pump drive from the human-machine interaction unit via the control host and a connector connected to the control host.

Compared with the existing technology, embodiments of the present application implement the method of uninterrupted power switching for a pump drive provided by the present application through the system. The control command input from the outside is transmitted to the pump drive via the human-machine interaction unit, the control host, and the connector connected to the control host. The operating parameters and alarm information of the pump drive are displayed on the display unit. The system provided by the present application can operate the method set forth in the first aspect, thereby avoiding false alarms of the system.

BRIEF DESCRIPTION OF THE DRAWINGS

The drawings described herein are provided for a further understanding of the present application and constitute a part of the present application. The illustrative embodiments of the present application and the descriptions thereof are used to explain the present application and do not constitute undue limitations on the present application. Some specific embodiments of the present application will be described in detail below by way of example and not limitation with reference to the drawings. The same reference numerals in the drawings indicate the same or similar components or parts. It should be understood by a person skilled in the art that the drawings are not necessarily drawn to scale. In the drawings.

DESCRIPTION OF THE EMBODIMENTS

To enable a person skilled in the art to better understand the solutions of the present application, the technical solutions in the embodiments of the present application will be clearly and completely described below in conjunction with the accompanying drawings in the embodiments of the present application. Obviously, the described embodiments are merely some rather than all of the embodiments of the present application. Based on the embodiments in the present application, all other embodiments obtained by a person of ordinary skill in the art without creative effort shall fall within the scope of protection of the present application.

An uninterrupted power supply switching method and system for a pump drive according to the present application can be applied in the field of ECMO (Extracorporeal Membrane Oxygenation), but are not limited to the field of ECMO (Extracorporeal Membrane Oxygenation). The ECMO system includes an oxygenator, a blood pump, a pump drive (device to be powered), and a power supply device(s), where the power supply device(s) may be a control host and/or a battery. The present application aims to solve the technical problem that the pump drive does not experience power interruption or abnormality alarm during a switching process between the control host and the battery.

Figure 1:
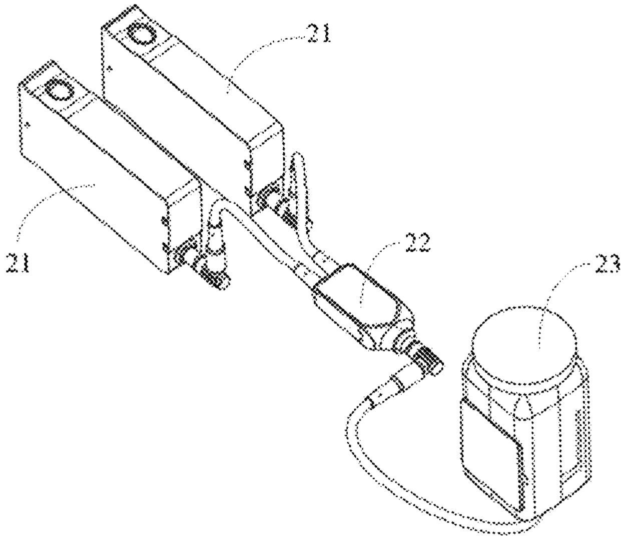
FIG. 1 is a schematic diagram of a partial physical connection structure of a system provided in an embodiment of the present application.
Figure 7:
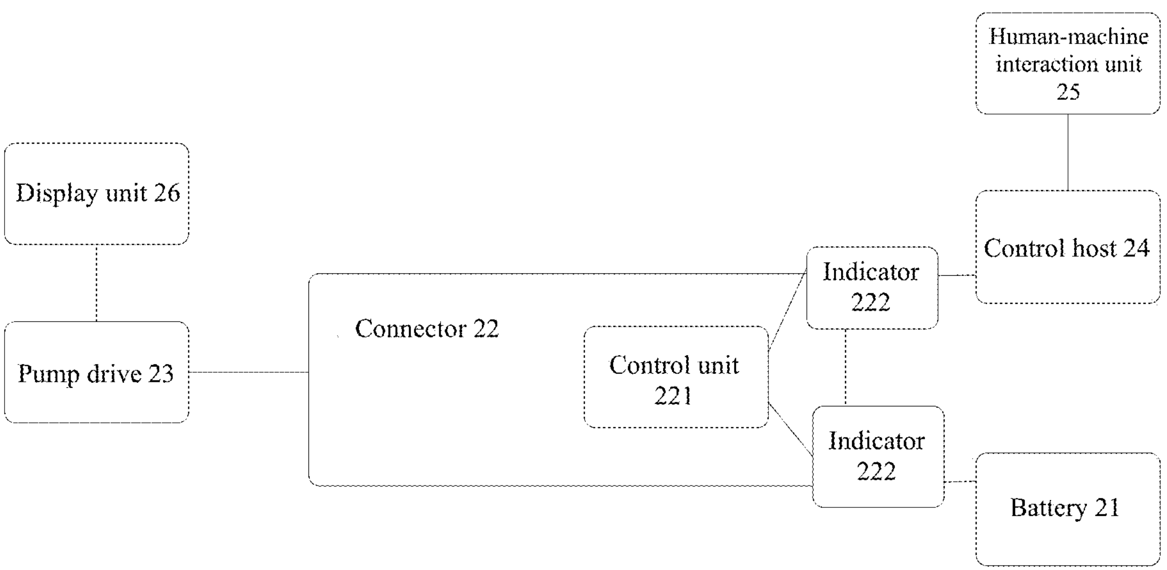
FIG. 7 is a schematic diagram of a system connection structure provided by an embodiment of the present application.

The method is applied to a system, as shown in FIG. 1, the system includes one or more power supply devices 21, a pump drive 23, a connector 22, and a display unit (shown in FIG. 7). The one or more power supply devices are electrically connected to the pump drive 23 via the connector 22 to supply power to the pump drive 23. The pump drive 23 is connected to the display unit. The power supply device 21 can be a control host or a battery.

Figure 2:
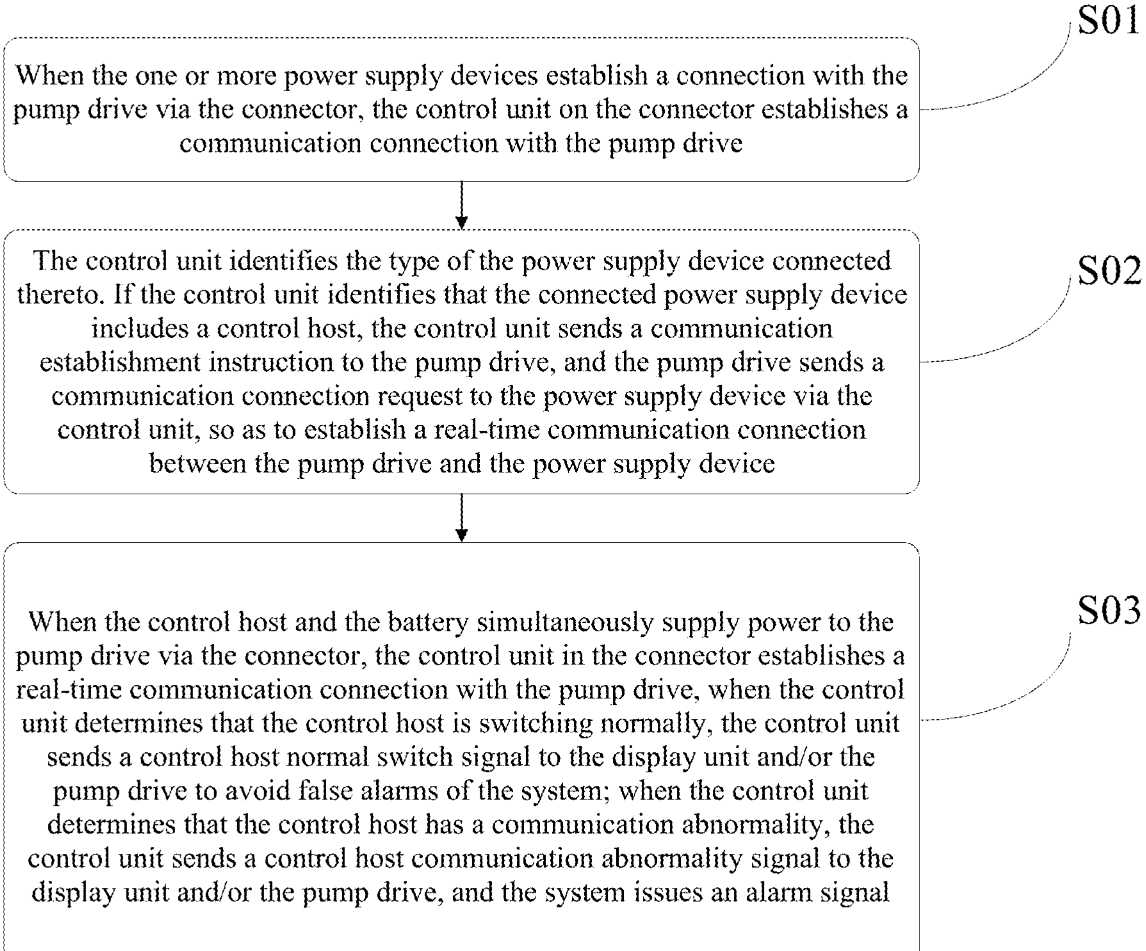
FIG. 2 is a schematic flow diagram of a method for uninterrupted power switching for a pump drive provided in an embodiment of the present application.

In a first aspect, as shown in FIG. 2, an embodiment of the present application provides an uninterrupted power supply switching method for a pump drive, which specifically includes the following steps:

Step S01: when the one or more power supply devices establish a connection with the pump drive via the connector, the control unit on the connector establishes a communication connection with the pump drive.

It should be noted that the control unit is arranged in the connector. When the one or more power supply devices are connected to the pump drive via the connector, the control unit on the connector starts to operate and establishes a communication connection with the pump drive.

In the embodiments of the present application, the control host is a component of the entire ECMO system, mainly used for monitoring the operating status of the entire ECMO system and supplying power to the pump drive. The control unit is arranged in the connector, and a detection control circuit is provided in the control unit. The control unit is mainly used to monitor the communication status between the control unit and the pump drive and monitor the power supply status of the power supply device(s) with the detection and monitoring circuit.

Figure 3:
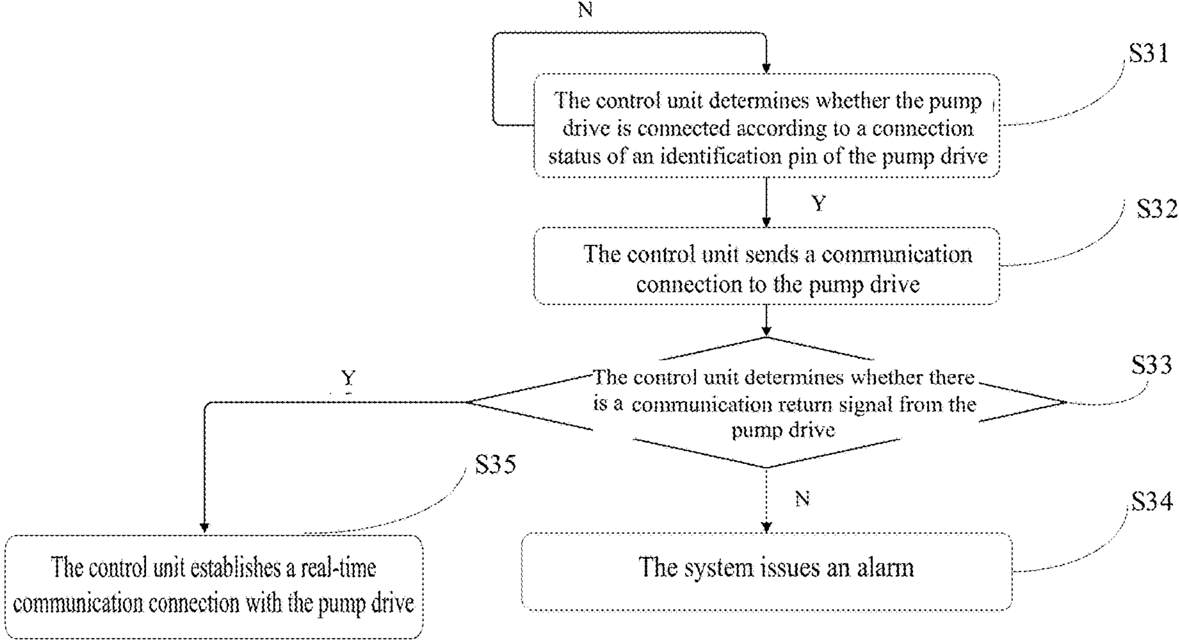
FIG. 3 is a flowchart of a control unit determining the connection status of a pump drive provided in an embodiment of the present application.

The control unit in the connector establishes a real-time communication connection with the pump drive, specifically including:

As shown in FIG. 3, first execute Step S31: the control unit determines whether the pump drive is connected according to a connection status of an identification pin of the pump drive. If it is yes, execute Step S32, where the control unit sends a communication connection to the pump drive; if it is not, continue executing Step S31.

Execute Step S33: the control unit determines whether there is a communication return signal from the pump drive. If it is yes, execute Step S35, the control unit establishes a real-time communication connection with the pump drive; if not, execute Step S34, the control unit sends a communication fault signal to the display unit, and the system issues an alarm to prompt troubleshooting.

It should be noted that the system issues an alarm specifically by means of an indicator provided on the connector controlled by the control unit, since at this time the control unit cannot establish communication with the pump drive, and therefore the control unit and the display unit also cannot establish communication, so the alarm can only be issued by the indicator on the connector.

Step S02: the control unit identifies the type of the power supply device connected thereto. If the control unit identifies that the connected power supply device includes a control host, the control unit sends a communication establishment instruction to the pump drive, and the pump drive sends a communication connection request to the power supply device via the control unit, so as to establish a real-time communication connection between the pump drive and the power supply device.

Figure 4:
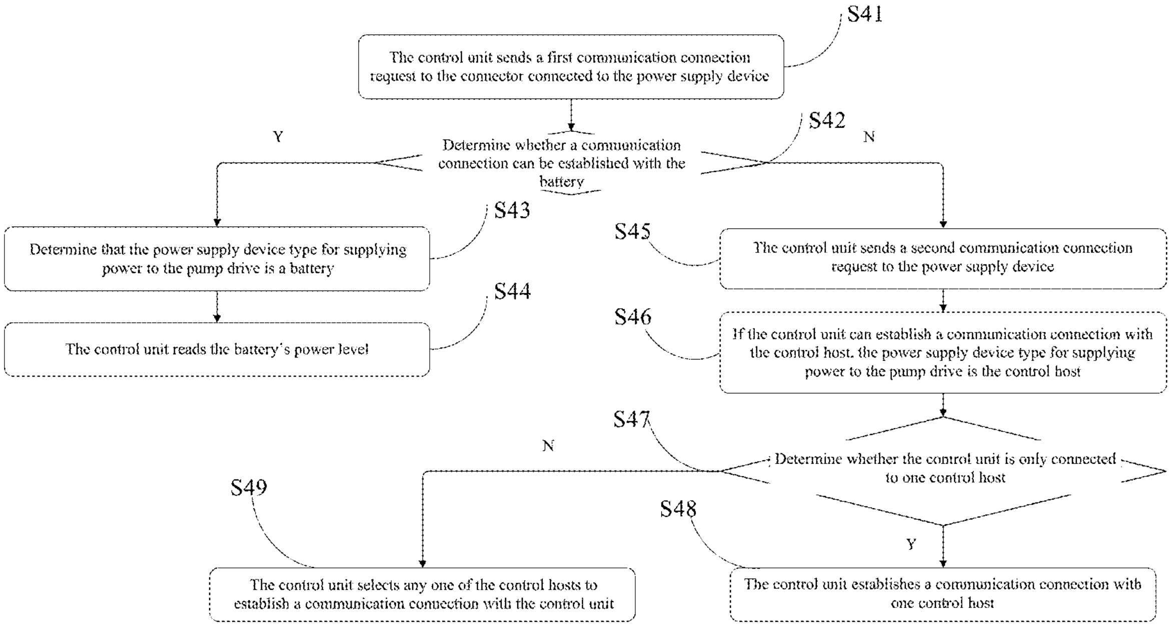
FIG. 4 is a flowchart of a control unit determining a power supply device connection status provided by an embodiment of the present application.

As shown in FIG. 4, step S02 specifically includes: first execute step S41; the control unit sends a first communication connection request to the connector connected to the power supply device; then execute step S42: determine whether the control unit can establish a communication connection with the battery, if the control unit can establish a real-time communication connection with the battery, then execute step S43: determine that the power supply device type for supplying power to the pump drive is a battery; then execute step S44: the control unit reads the battery's power level; it should be noted that, for the control unit to establish a real-time communication connection with the battery, as long as the control unit can read the corresponding parameter information of the battery, the control unit has established a real-time communication connection with the battery, and it is not necessarily required that the battery actively sends information to the control unit, waiting for the control unit to determine whether to return a response message to confirm that the control unit has established a real-time communication connection with the battery.

If the control unit cannot establish a communication connection with the battery, then execute step S45: the control unit sends a second communication connection request to the power supply device; then execute step S46: if the control unit can establish a communication connection with the control host, then the power supply device type for supplying power to the pump drive is the control host; then execute step S47: determine whether the control unit is only connected to one control host; if it is only connected to one control host, then execute step S48: the control unit establishes a communication connection with one control host, if it is not only connected to one control host, then execute step S49, the control unit selects any one of the control hosts to establish a communication connection with the control unit.

In the embodiments of the present application, when the control unit of the connector determines that the power supply device has a voltage output, the control unit of the connector sends a communication connection request to the power supply device to determine whether the power supply device is a battery or a control host. This is because the communication types between the control host and the battery with the control unit are different. For example, the control host in the present application uses CAN bus communication, and the battery uses $I^2C$ communication. The type of connected power supply device can be distinguished through these two communication types. Of course, the type of power supply device can also be identified through identification codes in the communication. $I^2C$ communication (Inter-Integrated Circuit) is a serial communication bus.

In the embodiments of the present application, an identification code can also be provided in the communication protocol between the control unit and the power supply device to determine the power supply type, because the identification code is set to correspond one-to-one with the specific type of the power supply device.

Step S03: when the control host and the battery simultaneously supply power to the pump drive via the connector, the control unit in the connector establishes a real-time communication connection with the pump drive, when the control unit determines that the control host is switching normally, the control unit sends a control host normal switch signal to the display unit and/or the pump drive to avoid false alarms of the system; when the control unit determines that the control host has a communication abnormality, the control unit sends a control host communication abnormality signal to the display unit and/or the pump drive, and the system issues an alarm signal.

It should be noted that normal switching refers to manual operations such as actively switching the control host to the battery or switching the battery to the control host. Basically, any manual operation to switch the power supply device will be identified and determined by the system as a normal switch. Whether the timing of the manual switching is reasonable is not within the scope of identification and determination provided by the system in the present application.

It should be noted that avoiding false alarms in the system may be achieved as the display unit and/or the pump drive receive the control host normal switch signal sent by the control unit and process it as a non-abnormal situation. Therefore, it could be that the display unit and/or the pump drive do not issue any alarms or prompts and continue to operate.

Moreover, the alarm signal issued by the system may be an alarm signal issued by the display unit and/or the pump drive, or it may be an alarm signal issued by other connected components of the system. The alarm signal may be sound, light, displayed icon characters, or even include some prompt messages. In short, any information that can be used to alert a user(s) falls within the scope of the alarm signal set forth in the present application.

The control unit determines that the control host is normally switched, including:

When the control unit detects that the communication between the control host and the control unit is disconnected within a preset time, and the power supply voltage of the connector connected to the control host is lower than a preset value or is 0, the control unit determines that the control host is normally switched and sends the control host normal switch signal to the display unit and/or the pump drive.

The control unit determines that the control host has a communication abnormality, including:

When the control unit detects that the communication between the control unit and the control host is disconnected within a preset time, and there is a power supply voltage at the connector connected to the control host, the control unit determines that the control host has a communication abnormality, and the control host supplies power to the pump drive normally;

The control unit sends the control host communication abnormality signal to the display unit and/or the pump drive.

In the embodiments of the present application, when determining whether the connector connected to the control host has a power supply voltage, it is mainly achieved by the following method: a power level monitoring circuit is provided between the connector and the power supply device, the power level monitoring circuit is electrically connected to the control unit, and the voltage at an input end of the power supply device is monitored by the power level monitoring circuit. The power level monitoring circuit uses a voltage divider resistor(s) for monitoring, and the monitored voltage signal is output to the control unit. The control unit determines whether this voltage meets the usage requirements of the device to be powered, and if not, it will issue an abnormality alarm.

After the connector establishes a connection with the power supply device, the control unit in the connector sends an instruction to a chip in the battery to read the power supply information. The control unit of the connector determines whether there is a power supply voltage at the connector connected to the control host based on whether there is a voltage signal output on the power supply device.

More specifically, when the control unit detects a switching change in the power supply device, the control unit performs a switching state determination. When it is confirmed that the switching requirements are met, the control unit sends normal switching information to the display unit and/or the pump drive.

If only the communication disconnection of the control host is detected while the power supply voltage still exists, it indicates that the power supply connector of the control host has not been unplugged for switching, and there is a communication abnormality between the control unit and the control host. In this case, the control unit can send the corresponding communication abnormality signal to the display unit and/or the pump drive, and the system can issue the corresponding alarm to alert an operator to check and troubleshoot the fault.

The control unit in the connector establishes a real-time communication connection with the pump drive. Once the power supply device is disconnected due to switching, the control unit immediately identifies the disconnection of the power supply device. When the control unit identifies the disconnection of the control host, it will monitor whether the corresponding power supply connector has no voltage supply. If so, it indicates that the power supply connector of the control host has been completely disconnected. Thus, it can be determined that the control host is actively switched by the operator, and a signal indicating that the control host is normally switched can be sent to the display unit and/or the pump drive.

The present application can enable uninterrupted operation of the pump drive power supply switching in the ECMO system, and at the same time identify the type and status of the power supply device, establish a communication connection, and when the power supply device is normally switched, it can be determined by the method of the present application and timely notify the display unit and/or the pump drive, effectively avoiding false alarms of the system.

In another embodiment of the present application, the method further includes:

When the power supply device supplying power to the pump drive includes a battery, the control unit reads battery parameters and calculates a battery endurance parameter based on the battery parameters, and sends the battery endurance parameter to the display unit;

When the battery endurance parameter is less than a preset threshold, the display unit issues an alarm to prompt troubleshooting.

Figure 5:
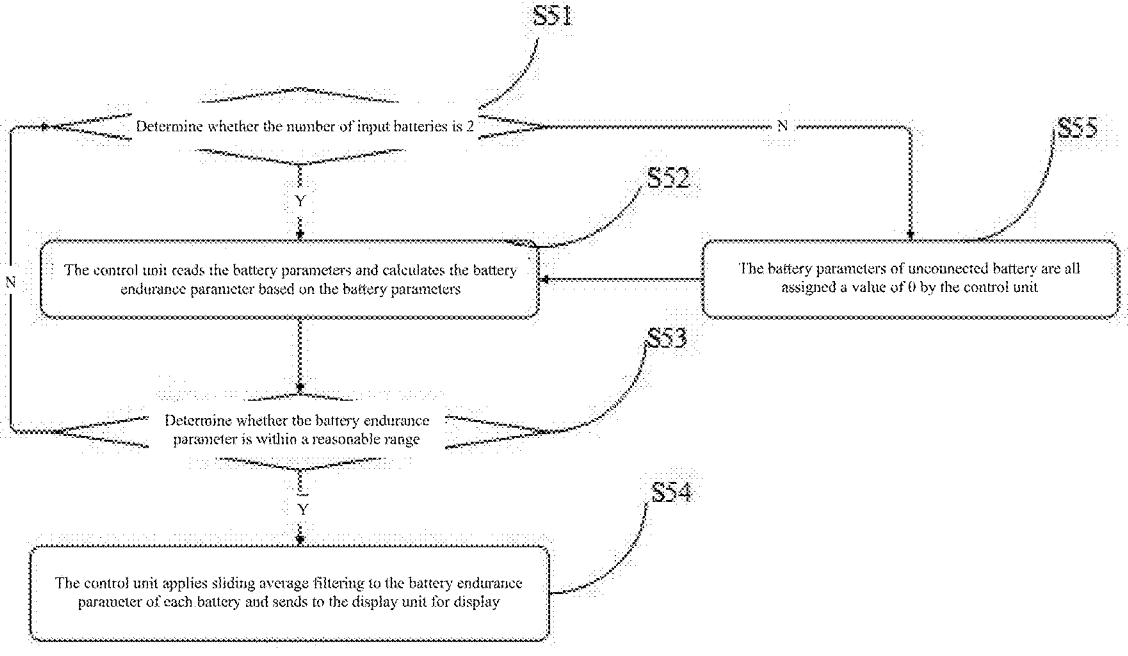
FIG. 5 is a flowchart of a control unit estimating remaining battery time and remaining battery percentage provided by an embodiment of the present application.

As shown in FIG. 5, the method further includes:

When the power supply device supplying power to the pump drive includes a battery, step S51 also needs to be performed to determine whether the number of input batteries is 2; if it is determined that the number of input batteries is not 2, step S55 is executed, and the battery parameters of unconnected battery are all assigned a value of 0 by the control unit. The control unit reads the battery parameters and calculates the battery endurance parameter based on the battery parameters.

If the number of input batteries is 2, step S52 is executed, and the control unit reads the battery parameters and calculates the battery endurance parameter based on the battery parameters.

The method for calculating the battery endurance parameter is as follows:

The control unit respectively reads the remaining capacity, total capacity, and output current of the battery, and then uses the following formulas to calculate the battery's remaining power supply time and remaining capacity percentage:

Battery remaining time=the sum of the remaining capacity of each battery=the sum of the output current of each battery;

Battery remaining capacity percentage=remaining capacity of the battery=total capacity of the battery.

Based on the above steps to obtain the battery endurance parameters, step S53 needs to be then executed, where the control unit determines whether the battery endurance parameter is within a reasonable range.

If the battery endurance parameter is within a reasonable range, step S54 is then executed, where the control unit applies sliding average filtering to the battery endurance parameter of each battery and sends to the display unit for display; if the battery endurance parameter is not within a reasonable range, return and continue to execute step S51 to re-read the battery capacity.

More specifically, in the embodiments of the present application, the total remaining time of the battery is calculated by adding the remaining capacity of each battery and then dividing by the sum of each battery output current. If the control unit detects that only one battery is connected, it does not need to read the parameters of other batteries and directly assigns the remaining capacity, total capacity, and output current of the other batteries a value of 0. This simplifies the calculation logic by assigning a value of 0.

The above mainly describes the method for calculating the battery endurance parameters. In other words, when the control unit of the connector detects that the power supply device has a battery supplying power to the pump drive, the control unit reads the battery parameters, calculates the battery endurance parameter based on the battery parameters, and sends the battery endurance parameter to the display unit.

More specifically, the control unit can access and read parameters such as the remaining capacity, total capacity, and output current of each battery through communication, and then calculate the battery endurance parameter of each battery based on these battery parameters. The battery endurance parameter is then sent to the display unit to inform the user of the accurate battery endurance time. Since a chip dedicated to battery power management is provided inside the battery, it can accurately measure the charging and discharging state through memory training and calculate the total capacity and remaining capacity of the battery. Compared with the conventional method of calculating battery capacity through battery discharge voltage, this is more accurate. Therefore, reading the battery endurance parameter can more accurately estimate the battery discharge time.

In addition, it is almost impossible for a large deviation between the calculated battery endurance parameters and the actual values to occur, which may be caused by abnormal battery parameter readings. For example, the remaining battery time may be far from the actual value, or the battery remaining percentage may exceed 100%. Through a simple judgment, such abnormal data can be filtered out. In addition, a sliding average filtering process can also be applied, which can make the calculation result more accurate.

The pump drive uninterrupted power supply switching method provided in the present application can meet the usage scenario of uninterrupted switching of the ECMO pump drive and can avoid false alarms being triggered during a switching process.

Figure 6:
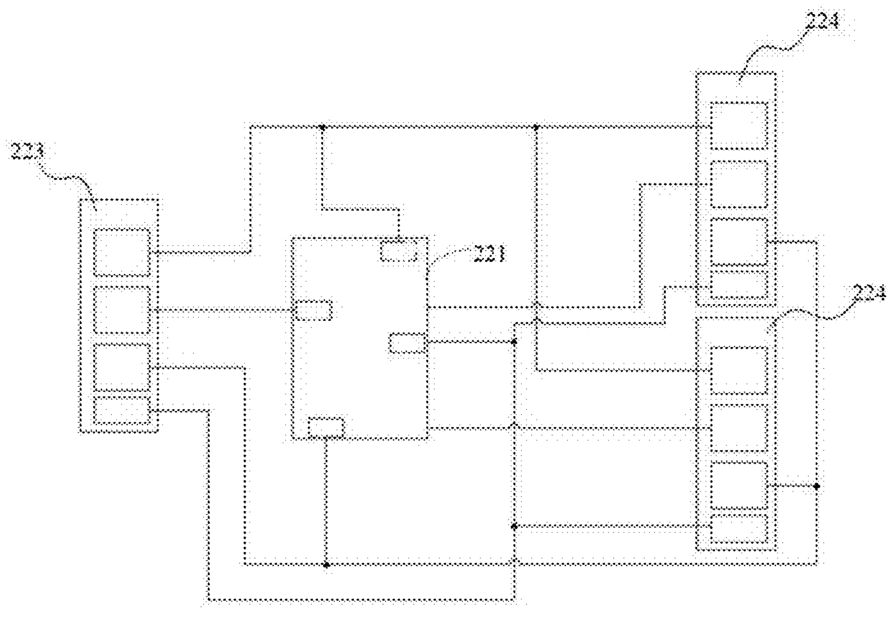
FIG. 6 is a schematic diagram of an uninterruptible switching circuit connection of a connector provided by an embodiment of the present application.

Moreover, it should be noted that, as shown in FIG. 6, in a first aspect, an uninterrupted power supply switching method for a pump drive is provided, which can be implemented by an uninterruptible switching circuit. The uninterruptible switching circuit is provided in the connector 22. The uninterruptible switching circuit includes a control unit 221, an output connector 223, and at least two power supply connectors 224. The output connector 223 is connected to a device to be powered 23 (i.e., the pump drive), and the at least two power supply connectors 224 are respectively connected to power supply devices 21. The output connector 223 is connected to the at least two power supply connectors 224, so that the power supply devices 21 connected to the at least two power supply connectors 224 can supply power to the device to be powered 23 (i.e., the pump drive) connected to the output connector 223. The control unit 221 is respectively connected to the output connector 223 and the at least two power supply connectors 224. When the device to be powered 23 (i.e., the pump drive) is disconnected from a power supply device 21, the control unit 221 determines whether another power supply device 21 connected to the power supply connectors 224 is supplying power normally to the device to be powered 23 (i.e., the pump drive) connected to the output connector 223. If so, the control unit 221 feeds back a normal power supply signal from the power supply device 21 to the device to be powered 23, thereby avoiding an abnormality alarm issued by the device to be powered 23 (i.e., the pump drive). By means of the control unit 221, the output connector 223, and the power supply connectors 224, the device to be powered 23 (i.e., the pump drive) and the power supply devices 21 are connected together. The output connector 223 is connected to the device to be powered 23, and the power supply connectors 224 are respectively connected to the power supply devices 21, so that multiple power supply devices 21 can simultaneously supply power to the device to be powered 23 (i.e., the pump drive), and the power supply devices 21 can be freely switched therebetween, thereby realizing uninterrupted power supply to the device to be powered 23 (i.e., the pump drive). In addition, by providing the control unit 221, the device to be powered 23 (i.e., the pump drive) can be respectively in communication connection with the multiple power supply devices 21, and the control unit 221 determines the connection status between the device to be powered 23 and the power supply devices 21, and feeds it back to the device to be powered 23 (i.e., the pump drive), thereby avoiding an abnormality alarm of the device 23 to be powered (i.e., the pump drive) during or after a switching process. The output connector 223 adopts a female connector with waterproof function; the power supply connectors 224 adopt male connectors with waterproof function.

Figure 8:
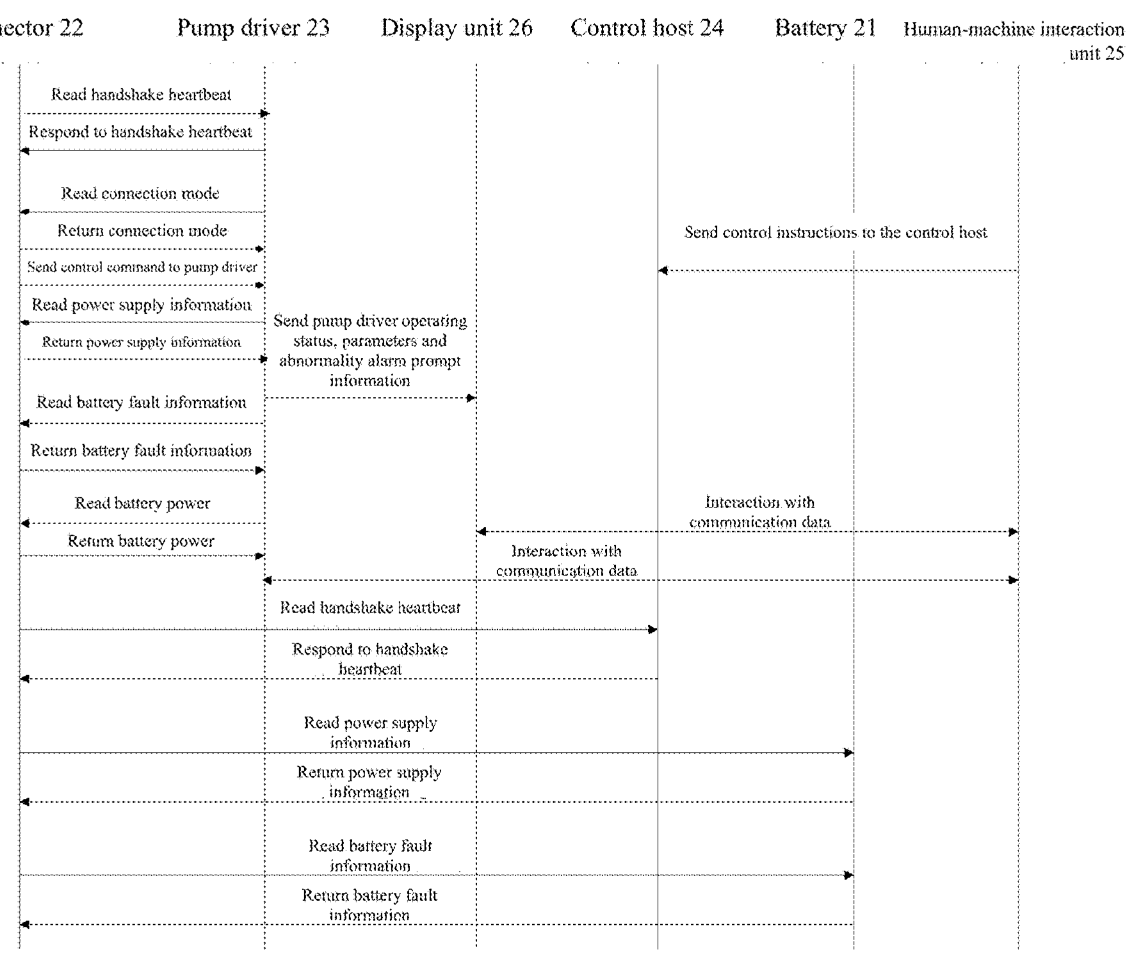
FIG. 8 is a schematic diagram of an information interaction process among components in a system provided by an embodiment of the present application.

In a second aspect, as shown in FIGS. 7 and 8, an embodiment of the present application further provides a system, the system being used to execute the method according to any one of the first aspect. The system includes a control host 24, a battery 21, a pump drive 23, a connector 22, a display unit 26, and a human-machine interaction unit 25. The control host 24 and the battery 21 are electrically connected to the pump drive 23 respectively via the connector 22. The pump drive 23 is connected to the display unit 26. The display unit 26 is configured to display the operating status, operating parameters, and abnormality alarm information of the pump drive 23.

The human-machine interaction unit 25 is electrically connected to the control host 24. Through the human-machine interaction unit 25, control commands input from the outside can be transmitted to the pump drive 23 via the control host 24 and the connector 22 connected to the control host 24. In addition, the human-machine interaction unit 25 can directly perform communication data interaction with the pump drive 23 and the display unit 26.

In the embodiments of the present application, the pump drive 23 is a power device of the ECMO system, providing power for extracorporcal blood circulation. Power outage and pump stoppage during operation can cause serious harm to a patient. The pump drive device is provided with cables connected to the outside, which can be used for power supply and communication connection. In some pump drives 23, the display unit 26 is built-in and can directly display the operating status and abnormality alarm information of the pump drive 23. Of course, for some pump drives 23, an independently connected display unit 26 can be provided. The pump drive 23 can be in communication connection with the display unit 26. The display unit 26 is mainly used to display the operating status, parameters, and abnormality alarm prompt information of the pump drive 23.

The connector 22 is a connection device for the power supply switching process of the pump drive 23, which can ensure that the pump drive 23 does not experience power outage or pump stoppage. Between the connector 22 and the pump drive 23, the connector 22 reads the handshake heartbeat from the pump drive 23, and then the pump drive 23 responds to the handshake heartbeat to establish and confirm a stable communication connection between the pump drive 23 and the connector 22. At the same time, the pump drive 23 reads the connection mode of the power supply device from the connector 22, and the connector 22 returns the connection mode of the power supply device. According to the connection mode of the power supply device, the pump drive 23 reads the power supply information, and the connector 22 returns the power supply information. If the power supply device fails, the pump drive 23 reads the fault information, and the connector 22 returns the fault information of the power supply device. The pump drive 23 reads the power level of the power supply device, and the connector 22 also returns the current level of the power supply device.

If the power supply device is the control host 24, the connector 22 reads the handshake heartbeat from the control host 24, and then the control host 24 responds to the handshake heartbeat to establish communication between the control host 24 and the connector 22.

If the power supply device is the battery 21, the connector 22 reads the power supply information from the battery 21, and the battery 21 returns the power supply information. If the battery 21 fails, the connector 22 reads the fault information, and the battery 21 returns the fault information of the power supply device. It should be noted that, usually when the battery 21 fails, the connector 22 cannot read the communication signal, so the control unit 221 of the connector 22 returns fault information. Of course, some batteries 21 may send some battery fault information even when an internal fault occurs.

As shown in FIG. 6, the connector 22 includes three movable quick-detach connectors that can be used for power supply and communication electrical connection, namely two power supply connectors 224 and one output connector 223. The output connector 223 is connected to the pump drive 23 by a cable, and the two power supply connectors 224 are respectively connected to power supply devices, i.e., the control host 24 and the battery 21. The structures and functions of the two power supply connectors 224 are completely identical and can both be connected to either the control host 24 or the battery 21. A control unit 221 is provided inside the connector 22, which can connect the power supply and communication circuits input from the two power supply connectors 224 to the output connector, thereby providing redundant power supply and communication connection for the pump drive 23. An indicator 222 can be provided at the respective positions corresponding to the two power supply connectors 224. The indicators 222 are respectively controlled by the control unit 221 and can emit prompting lights or information. By way of flashing of the indicator 222 at a certain frequency or emitting abnormal prompts in different colors, it can also send system communication fault alarm information to the pump drive 23, which will then issue an alarm.

The battery 21 is one of the power supply devices for the pump drive 23 and can be connected to either one or both of the two power supply connectors 224. It is internally equipped with power monitoring, capable of calculating and outputting real-time remaining power, output current, total capacity of the battery 21, as well as other battery parameter information. It uses $I^2C$ communication connection or other communication modes with external devices, which are not limited in the embodiments of the present application.

The control host 24 is one of the power supply devices for the pump drive 23 and can be connected to either one or both of the two power supply connectors 224. The control host 24 can provide power for the entire ECMO system. It may receive AC or DC power input from an external power source, and after conversion, provide continuous power supply to the entire system and the pump drive device. It may also be internally equipped with a backup battery power supply. The control host 24 is provided with a connection port that can be electrically connected to the display unit 26. Communication between the control host 24 and both the pump drive 23 and the display unit 26 is carried out using the CAN bus communication.

The connector 22 is connected to the pump drive 23, the pump drive 23 is connected to the display unit 26, the control host 24 is connected to the connector 22, the battery 21 is connected to the connector 22, and the control host 24 is connected to the human-machine interaction unit 25.

The control host 24 and/or the battery 21 can each supply power to the pump drive 23 via the connector 22, while also ensuring normal communication connections between the various components. The connector 22 plays a monitoring and communication role throughout the entire switching process, ensuring safer and more reliable power supply switching for the ECMO system pump drive without interrupting its operation.

Figure 9:
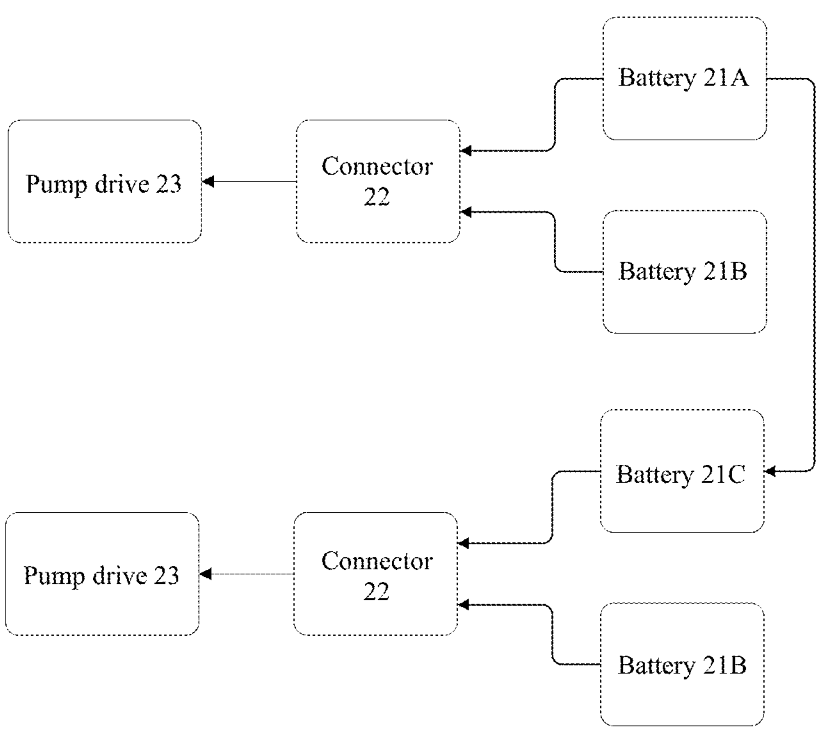
FIGS. 9 to 11 are state diagrams of different state transitions of a power supply device(s) provided by an embodiment of the present application.

The specific switching operations for various application scenarios are as follows:

As shown in FIG. 9, the switch from a battery 21A→a battery 21C is as follows: when the ECMO system is powered by two batteries 21A and 21B in an emergency situation, if the power level of the battery 21A is low, it needs to be replaced with a battery 21C; at this time, the battery 21A can be disconnected from a pump drive 23, and the pump drive 23 is then powered by the battery 21B and thus can still operate normally. A connector 22 detects that there is no voltage input at a connector corresponding to the battery 21A, and a corresponding indicator 222 displays a power disconnection status, the battery power information is updated, which is then sent to a display unit 26 for display; when the new battery 21C is connected, the voltage input at a connector corresponding to battery 21C can be detected, and the corresponding indicator 222 then display a power connection status. The battery power information is then updated again according to the above process and sent to the display unit 26 for display, thus completing the switching.

Figure 10:
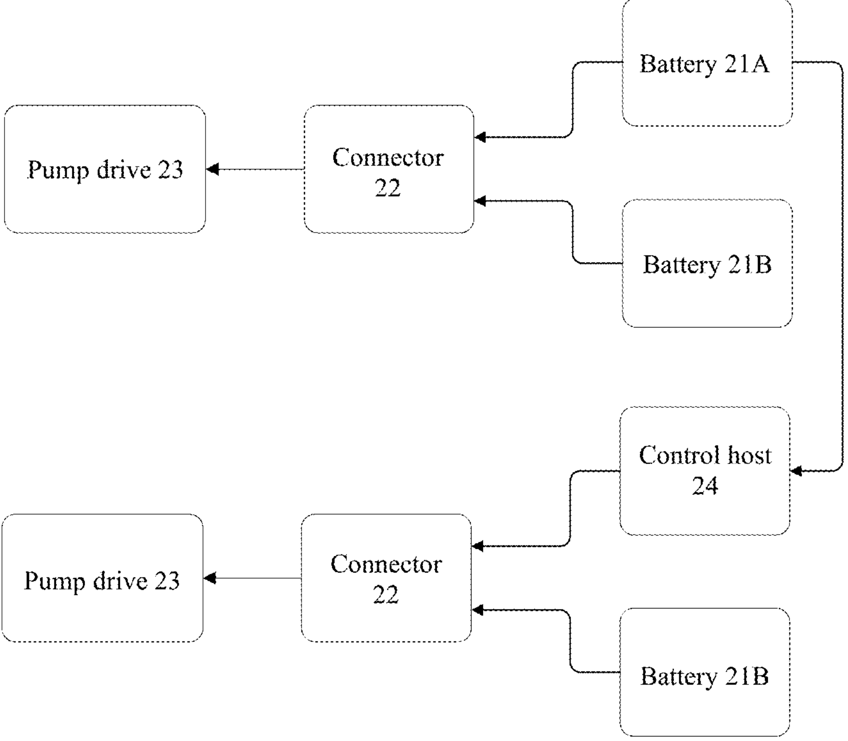

As shown in FIG. 10, the switch from the battery 21A→a control host 24 is as follows: when the ECMO system is powered by two batteries 21A and 21B in an emergency situation, as the emergency mode ends, the battery 21A needs to be replaced to supply power to the control host 24. At this time, the battery 21A can be disconnected from the drive device. The pump drive 23 is then powered by the battery 21B and can still operate normally. An uninterrupted switching device detects that there is no voltage input at the connector corresponding to battery 21A, and the corresponding power supply indicator 222 then displays a power disconnection status. The battery power information is thus updated according to the above process and sent to the display unit 26 for display; when the new control host 24 is connected, the voltage input at a connector corresponding to the new control host 24 can be detected, and the corresponding indicator 222 then displays a power connection status. The display unit 26 then notifies the pump drive 23 to establish a communication connection with the control host 24. After the pump drive 23 establishes a communication connection with the control host 24, since the pump drive 23 does not detect a new battery being connected at that time, the battery power update belongs to a regular real-time change; only after the communication connection with the control host 24 is established, the battery information in the control host 24 can be read, and then the battery power information is updated. The switching operation to the control host 24 is then completed.

Figure 11:
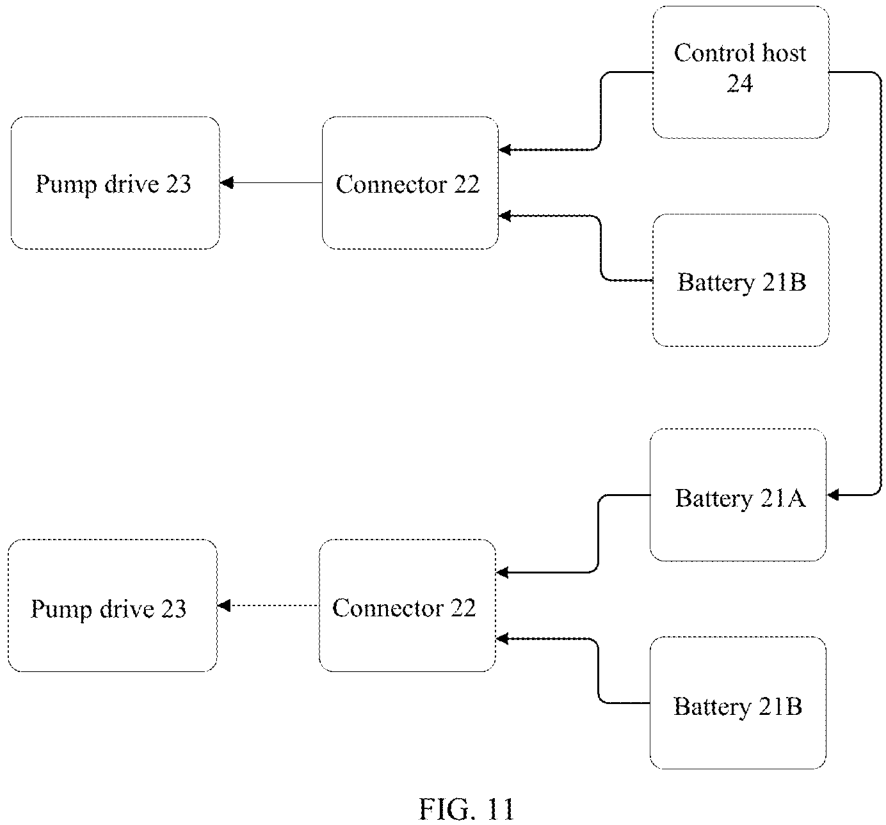

As shown in FIG. 11, the switch from the control host 24→the battery 21A is as follows: when the ECMO system is in normal operation and the pump drive 23 is powered by one battery 21B and the control host 24, due to the need to switch to a transport mode, the control host 24 needs to be replaced with the battery 21A for power supply. At this time, the control host 24 can be disconnected from the pump drive 23. The pump drive 23 then relies on the battery 21B for power supply and can still operate normally. The connector 22 can detect that there is no voltage input at the connector corresponding to the control host 24, and the corresponding power supply indicator 222 will display a power disconnection status. Meanwhile, real-time communication monitoring can detect a communication abnormality and identify that the control host 24 is undergoing a normal switch, and thus issues a command to the pump drive 23 to stop sending abnormality alarm information; when the battery 21A is connected, the voltage input at the connector corresponding to battery 21A can be detected, and the corresponding power supply indicator 222 will display a power connection status. The battery power information is then updated again according to the above process and sent to the display unit 26 for display, thereby completing the switching operation.

The above three switching scenarios are relatively typical application switches and represent scenarios of normal manual switching between power supply devices as applied in the embodiments of the present application. Through combinations of these three switching scenarios, more switching scenarios can be derived, all of which can be monitored and identified by the method of the present invention, distinguishing between normal and abnormal switches, and issuing timely alarms to alert the operator in the event of an abnormal switch. The present application, through various logical determinations, distinguishes and identifies normal and abnormal switches, thereby accommodating flexible and variable application scenario changes.

Finally, it should be noted that the above embodiments are merely used to illustrate the technical solutions of the present application, and not to limit them; although the present application has been described in detail with reference to the foregoing embodiments, a person skilled in the art should understand that modifications may still be made to the technical solutions described in the foregoing embodiments, or equivalent replacements may be made to some or all of the technical features therein; and these modifications or replacements do not cause the essence of the corresponding technical solutions to depart from the scope of the technical solutions of the embodiments of the present application.

What is claimed is:

1. An uninterrupted power supply switching method for a pump drive system, the system comprising one or more power supply devices, a pump drive, a connector, and a display unit, wherein the one or more power supply devices are electrically connected to the pump drive via the connector for supplying power to the pump drive, wherein the pump drive is connected to the display unit, and wherein the power supply devices comprise a control host or a battery, the method comprising:

establishing, by the control unit, a communication connection with the pump drive;

establishing, by the one or more power supply devices, a connection with the pump drive via the connector in response to the connector establishing a communication connection with the pump drive;

identifying, by the control unit, a type of a power supply device connected thereto;

sending, by the control unit, a communication establishment instruction to the pump drive in response to the control unit identifying that the connected power supply device comprises a control host;

sending, by the pump drive, a communication connection request to the power supply device via the control unit to establish a real-time communication connection between the pump drive and the power supply device in response to the control unit identifying that the connected power supply device comprises a control host;

establishing, by the control unit, a real-time communication connection with the pump drive in response to the control host and the battery simultaneously supplying power to the pump drive via the connector;

switching between the control host and the battery;

sending, by the control unit, a control host normal switch signal to the display unit and the pump drive to avoid a false alarm of the system in response to the control unit determining that the control host is switched normally;

sending, by the control unit, a control host communication abnormality signal to the display unit and the pump drive in response to the control unit determining that the control host has a communication abnormality; and issuing, by the system, an alarm signal in response to the control host communication abnormality signal.

2. The uninterrupted power supply switching method for a pump drive according to claim 1, wherein the control unit determines that the control host is switched normally, the uninterrupted power supply method further comprising:

detecting by the control unit that communication between the control host and the control unit is disconnected within a preset time, and a power supply voltage of the connector connected to the control host is lower than a preset value or is 0;

determining, by the control unit, that the control host is switched normally; and sending, by the control unit, the control host normal switch signal to the display unit and/or the pump drive.

3. The uninterrupted power supply switching method for a pump drive according to claim 1, wherein the control unit determines that the control host is switched abnormality, the uninterrupted power supply method further comprising:

detecting, by the control unit, that communication between the control unit and the control host is disconnected within a preset time, and there is a power supply voltage at the connector connected to the control host;

determining that the control host has a communication abnormality and the control host is supplying power to the pump drive normally; and sending, by the control unit, the control host communication abnormality signal to the display unit and/or the pump drive.

4. The uninterrupted power supply switching method for a pump drive according to claim 1, wherein the control unit identifies the type of the power supply device connected thereto, the uninterrupted power supply switching method further comprising:

sending, by the control unit, a first communication connection request to the connector connected to the power supply device;

determining, by the control unit establishing a real-time communication connection with the battery, the type of the power supply device supplying power to the pump drive to be the battery;

reading, by the control unit, a power level of the battery in response to determining the type of the power supply device to be the battery;

sending, by the control unit, a second communication connection request to the power supply device in response to the control unit failing to establish a communication connection with the battery determining, in response to the control unit establishing communication connection with the control host, that the type of the power supply device supplying power to the pump drive is the control host;

determining whether the control unit establishes a communication connection with only one control host, in response to the control unit establishing communication connection with the control host;

establishing, by the control unit, a communication connection with that one control host in response to establishing the communication connection with the only one control host;

selecting, by the control unit, any one of the control hosts to establish a communication connection with the control unit in response to establishing the communication connection with more than one control host.

5. The uninterrupted power supply switching method for a pump drive according to claim 1, wherein establishing, by the control unit, the real-time communication connection with the pump drive comprises:

determining, by the control unit, whether the pump drive is connected;

sending, by the control unit, a communication connection to the pump drive in response to determining that the pump drive is connected; and determining, by the control unit, whether the pump drive sent communication return signal; and establishing, by the control unit, the real-time communication connection with the pump drive in response to determining that the pump drive sent the communication return signal; and issuing an alarm in response to determining that the pump drive did not send the communication return signal.

6. The uninterrupted power supply switching method for a pump drive according to claim 1, wherein the power supply device supplying power to the pump drive comprises a battery, and the uninterrupted power supply switching method further comprises:

reading, by the control unit battery parameters;

calculating a battery endurance parameter based on the battery parameters;

sending the battery endurance parameter to the display unit; and issuing, by the display unit, an alarm to remind a user to check for faults in response to the battery endurance parameter being less than a present threshold.

7. The uninterrupted power supply switching method for a pump drive according to claim 6, wherein the power supply device supplying power to the pump drive comprises a battery, the uninterrupted power supply switching method further comprises:

determining whether the number of input batteries is two;

setting, by the control unit, all battery parameters of unconnected batteries to be zero in response to determining that the number of input batteries is not two;

reading, by the control unit, the battery parameters;

calculating, by the control unit, a battery endurance parameter based on the battery parameters;

reading, by the control unit, the battery parameters in response to determining that the number of input batteries is two; and calculating the battery endurance parameter based on the battery parameters in response to determining that the number of input batteries is two;

wherein calculating the battery endurance parameter comprises:

reading, by the control unit, a remaining capacity, a total capacity, and an output current of each battery, respectively; and calculating, by the control unit, a remaining power supply time and a remaining power percentage of the batteries, respectively, wherein:

the remaining power supply time equals a sum of remaining capacities of each battery divided by a sum of output currents of each battery; and the battery remaining power percentage equals a battery remaining capacity divided by a battery total capacity.

8. The uninterrupted power supply switching method for a pump drive according to claim 7, further comprising:

determining, by the control unit, whether the battery endurance parameter is within a reasonable range;

performing, by the control unit, sliding average filtering processing on the battery endurance parameter of each battery, respectively, in response to the battery endurance parameter being within the reasonable range;

sending to the display unit for display;

re-reading, by the control unit, the battery parameters of the battery corresponding to the battery endurance parameter that is not within the reasonable range in response to the battery endurance parameter not being within the reasonable range.

9. A system configured to perform the uninterrupted power supply switching method according to claim 1, wherein:

the system comprises a control host, a battery, a pump drive, a connector, a display unit, and a human-machine interaction unit;

the control host and the battery is electrically connected to the pump drive respectively via the connector;

the pump drive is connected to the display unit;

the display unit is configured to display an operating status, operating parameters, and abnormality alarm information of the pump drive; and the human-machine interaction unit is electrically connected to the control host; wherein a control instruction input from the outside is transmitted to the pump drive by means of the human-machine interaction unit via the control host; and the connector connected to the control host.

* * * * *